(12) United States Patent
Jan

(10) Patent No.: US 10,788,606 B2
(45) Date of Patent: Sep. 29, 2020

(54) OPHTHALMIC LENS AND METHOD FOR MANUFACTURING THE SAME

(71) Applicant: BenQ Materials Corporation, Taoyuan (TW)

(72) Inventor: Fan-Dan Jan, Taoyuan (TW)

(73) Assignee: BenQ Materials Corporation, Taoyuan (TW)

( * ) Notice: Subject to any disclaimer, the term of this patent is extended or adjusted under 35 U.S.C. 154(b) by 111 days.

(21) Appl. No.: 15/679,787

(22) Filed: Aug. 17, 2017

(65) Prior Publication Data

US 2018/0292575 A1 Oct. 11, 2018

(30) Foreign Application Priority Data

Apr. 10, 2017 (TW) .............................. 106111948 A

(51) Int. Cl.
| | |
|---|---|
| *G02B 1/04* | (2006.01) |
| *G02B 1/18* | (2015.01) |
| *A61L 27/52* | (2006.01) |
| *B29D 11/00* | (2006.01) |

(52) U.S. Cl.
CPC .............. *G02B 1/043* (2013.01); *A61L 27/52* (2013.01); *B29D 11/00067* (2013.01); *B29D 11/00865* (2013.01); *G02B 1/18* (2015.01); *A61L 2430/16* (2013.01)

(58) Field of Classification Search
CPC ........... G02B 1/043; G02B 1/18; A61L 27/52; A61L 2430/16; A61L 12/00; A61L 12/08; A61L 12/14; A61L 12/142; B29D 11/00067; B29D 11/00865
USPC ......... 351/159.02, 159.33, 178; 525/39, 32.1
See application file for complete search history.

(56) References Cited

U.S. PATENT DOCUMENTS

| | | | | |
|---|---|---|---|---|
| 2013/0118127 A1* | 5/2013 | Kolluru | ..................... | B65B 5/04 53/431 |
| 2014/0163133 A1* | 6/2014 | Chan | ..................... | A61L 27/227 523/105 |
| 2014/0336040 A1* | 11/2014 | Yan | ..................... | C08G 73/0688 502/159 |
| 2015/0057389 A1* | 2/2015 | Chauhan | ................ | G02B 1/043 523/107 |
| 2017/0362458 A1* | 12/2017 | Cheng | .................. | C07C 229/12 |

FOREIGN PATENT DOCUMENTS

| | | | | |
|---|---|---|---|---|
| CN | 1961242 | A | 5/2007 | |
| CN | 101128227 | A | 2/2008 | |
| CN | 102000658 | * | 4/2011 | ............... B05D 1/18 |
| CN | 102307955 | A | 1/2012 | |
| CN | 103214636 | A | 7/2013 | |
| CN | 104357814 | A | 2/2015 | |
| CN | 104524986 | A | 4/2015 | |
| CN | 104898189 | A | 9/2015 | |
| CN | 104936626 | A | 9/2015 | |
| CN | 205301735 | U | 6/2016 | |
| CN | 106501963 | A | 3/2017 | |

OTHER PUBLICATIONS

Polydopamine—a nature-inspired polymer coating for biomedical science, Nanoscale, 2011, 3, 4916 (Year: 2011).*
Structure, Properties and Applications of Mussel-Inspired Polydopamine Journal of Biomedical Nanotechnology, 2014 (Year: 2014).*
Colorless polydopamine coatings for creating functional interfaces, Kohri et al., Polymer Science: Research Advances, Practical Applications and Educational Aspects, Formatex Research Center, Lisbon (2016), pp. 159-168 (Year: 2016).*
Optimization of Polydopamine Coatings The University of Akron, Helen Terrill (Year: 2015).*

* cited by examiner

*Primary Examiner* — Travis S Fissel

(57) ABSTRACT

The invention is to provide an ophthalmic lens comprising a lens body, a polydopamine layer formed on the surface of the lens body and an antimicrobial layer bonded to the polydopamine layer, and manufacturing method thereof, wherein the antimicrobial layer is formed from a copolymer of carboxyl-containing polymer and zwitterionic polymer and a crosslinking agent, and the zwitterionic polymer can be selected from one of the group consisting of phosphorylcholine polymer, sulfobetaine polymer, carboxybetaine polymer and mixed-charge polymer or a combination thereof.

16 Claims, No Drawings

OPHTHALMIC LENS AND METHOD FOR MANUFACTURING THE SAME

CROSS-REFERENCE TO RELATED APPLICATION

This application claims the priority benefit of Taiwanese application serial No. 106111948, filed on Apr. 10, 2017, which is incorporated herein by reference.

BACKGROUND OF THE INVENTION

Field of the Invention

The present invention relates to an ophthalmic lens and a method for manufacturing the same. More particularly, the present invention relates to an ophthalmic lens with excellent deposit resistance, high antimicrobial properties, high hydrophilicity, desired optical properties and surface lubricity, and a method for manufacturing the same.

Description of Related Art

In the early years, hard contact lens was mainly made of glass. The soft contact lens was therefore developed to improve the wearing discomfort of the hard contact lens. The soft contact lens can be classified into two categories, hydrogel contact lens and silicone hydrogel contact lens.

The surface hydrophilicity of contact lens will increase the wearing comfort of contact lens. However, the increased surface hydrophobicity of the contact lens will increase the protein and lipid in the tears to deposit on the surface of the contact lens will result in reduction of the clarity of lens and the wearing comfort reduced and even the ocular allergy occurred. Moreover, the bacteria on 'user's finger is usually transferred to the soft contact lens and adhering thereon during wearing the contact lens, which will result in ocular infection thereafter. Therefore, there is a need for ophthalmic lens with high hydrophilicity, deposit resistance and antimicrobial properties.

Several methods have been proposed in the state of the art to solve the problem of protein and/or lipid deposition, such as adding fluoro-containing monomers or zwitterionic materials into the composition for manufacturing the ophthalmic lens; treating the surface of the contact lens by plasma treatment; or modifying the surface of contact lens by, for example, covalently bonding zwitterionic materials to the surface of the contact lens. The approaches mentioned above have various disadvantages. For example, it is known that the addition of fluoro-containing monomers to the composition for manufacturing the ophthalmic lens will lower the surface hydrophilicity of the formed lens; the addition of zwitterionic materials into the composition for manufacturing the ophthalmic lens will adversely affect the physical properties of ophthalmic lens and decrease the production yield; plasma treatment is conducted by high-cost equipment; the modification of lens surface will cause lens deformation and/or decrease the production yield and needs further cleaning step so that the manufacturing process thereof is complicated.

It is reported that polydopamine possesses a structure similar to the adhesive proteins secreted by mussel with amounts of hydrophilic hydroxy functional groups and amine functional groups. Therefore, polydopamine has been widely used in surface modification of medical instrument for improving hydrophilicity or biocompatibility, for example, the surface of catheters, implants or tissue scaffolds made of plastic, metal, ceramic or cloth. However, because polydopamine is in dark blue, the surface modified thereby will be in brown color. Thus, the conventional method for modifying surface of medical instrument by polydopamine is not suggested to be used on articles which require for unique optical properties. In addition, because polydopamine has great absorbability for biological cell and protein, polydopamine is not highly suggested to be used in ophthalmic lens due to the deposit resistance concerns.

Therefore, an object of the present invention is to provide an ophthalmic lens having a novel antimicrobial layer which provides excellent deposit resistance, high antimicrobial property, high hydrophilicity and desirable optical property, and a simple and high effective method for manufacturing the ophthalmic lens.

SUMMARY OF THE INVENTION

The present invention provides an ophthalmic lens. The present ophthalmic lens has a polydopamine layer and a novel antimicrobial layer, which provides excellent deposit resistance, high antimicrobial property, high hydrophilicity and desired optical properties and surface lubricity. The present ophthalmic lens comprises a polydopamine layer formed on a surface of the ophthalmic lens and a zwitterionic polymer bonded on the polydopamine layer by a crosslinking agent. By using crosslinking agent to increase the surface density of the zwitterionic polymer, the zwitterionic polymer can provide the contact lens with the resistance of protein and lipid deposition and bacteria adhesion to achieve an excellent deposit resistance and high antimicrobial properties. Moreover, the wearing comfortability of the present ophthalmic lens can be enhanced because the polydopamine provides a great biocompatibility and hydrophility and the protein in the tears will not deposit on the surface of the ophthalmic lens. Additionally, although the ophthalmic lens of the present invention comprises polydopamine and zwitterionic polymer, optical properties of the ophthalmic lens, such as the transmittance, can still be retained.

According to an aspect of the present invention, an ophthalmic lens is provided. The present ophthalmic lens comprises a lens body, a polydopamine layer and an antimicrobial layer. The polydopamine layer is adhered to the surface of the lens body and the antimicrobial layer is bonded to the polydopamine layer. The antimicrobial layer is formed from a copolymer of carboxyl-containing polymer and zwitterionic polymer and a crosslinking agent. The zwitterionic polymer can be selected from one of the group consisting of phosphorylcholine polymer, sulfobetaine polymer, carboxybetaine polymer and mixed-charge polymer or a combination thereof. The visible light transmittance of the present ophthalmic lens is not less than 92%.

In a preferred embodiment of the present invention, wherein the zwitterionic polymer is selected from one of the group consisting of poly(2-methacryloyloxyethyl phosphorylcholine) (PMPC), poly(sulfobetaine methacrylate) (PSBMA) and poly(carboxybetaine methacrylate) (PCBMA) or a combination thereof.

In a preferred embodiment of the present invention, wherein a weight average molecular weight of the copolymer of carboxyl-containing polymer and zwitterionic polymer is in the range of 10,000 to 500,000, and preferably in the range of 20,000 to 40,000.

In a preferred embodiment of the present invention, wherein the carboxyl-containing polymer is poly acrylic acid (PAA) and/or poly methacrylic acid (PMA).

In a preferred embodiment of the present invention, wherein the crosslinking agent is selected from one of the group consisting of 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin and copolymer of dimethylamine and epichlorohydrin or a combination thereof.

In a preferred embodiment of the present invention, wherein the lens body is made of a hydrogel or a silicon hydrogel.

According to another aspect of the present invention, a simple and high effective method for manufacturing an ophthalmic lens is provided. The ophthalmic lens manufactured by the method has excellent deposit resistance, high antimicrobial property, high hydrophilicity, desired optical properties and surface lubricity.

The method for manufacturing the ophthalmic lens comprises steps of: (a) providing a lens body, and immersing the lens body in a polydopamine solution to coat a polydopamine layer on a surface of the lens body; (b) washing the polydopamine-coated lens body; and (c) immersing the polydopamine-coated lens body in a solution containing a copolymer of carboxyl-containing polymer and zwitterionic polymer and a crosslinking agent to form an antimicrobial layer bonded to the polydopamine layer; wherein the zwitterionic polymer is selected from one of the group consisting of phosphorylcholine polymer, sulfobetaine polymer, carboxybetaine polymer and mixed-charge polymer or a combination thereof.

In a preferred embodiment of the method of the present invention, wherein the zwitterionic polymer is selected from one of the group consisting of poly(2-methacryloyloxyethyl phosphorylcholine) (PMPC), poly(sulfobetaine methacrylate) (PSBMA) and poly(carboxybetaine methacrylate) (PCBMA) or a combination thereof.

The method for manufacturing the ophthalmic lens can further comprise a step of preparing the polydopamine solution from dopamine in alkaline environments before the step of (a).

In a preferred embodiment of the method of the present invention, wherein the concentration of the polydopamine solution is in the range of 25 ppm to 500 ppm, and preferably in the range of 50 ppm to 300 ppm.

In a preferred embodiment of the method of the present invention, wherein the polydopamine solution is heated at the temperature in the range of 40° C. to 80° C., and preferably in the range of 50° C. to 70° C. in the step of (a).

In a preferred embodiment of the method of the present invention, wherein the lens body is immersed in the polydopamine solution for a time in the range of 5 minutes to 60 minutes, and preferably in the range of 10 minutes to 30 minutes in the step of (a).

In a preferred embodiment of the method of the present invention, wherein the concentration of the copolymer of carboxyl-containing polymer and zwitterionic polymer is in the range of 200 ppm to 2000 ppm, and preferably in the range of 300 ppm to 1000 ppm.

In a preferred embodiment of the method of the present invention, wherein the solution containing copolymer of carboxyl-containing polymer and zwitterionic polymer and the crosslinking agent is heated at the temperature in the range of 60° C. to 121° C., and preferably in the range of 70° C. to 121° C. in the step of (c).

In a preferred embodiment of the method of the present invention, wherein the polydopamine-coated lens body is immersed in the solution containing the copolymer of carboxyl-containing polymer and zwitterionic polymer and the crosslinking agent for a time in the range of 20 minutes to 90 minutes, and preferably in the range of 30 minutes to 60 minutes in the step of (c).

In a preferred embodiment of the method of the present invention, wherein the weight average molecular weight of the copolymer of carboxyl-containing polymer and zwitterionic polymer is in the range of 10,000 to 50,000, and preferably in the range of 20,000 to 40,000.

In a preferred embodiment of the method of the present invention, wherein the carboxyl-containing polymer is poly acrylic acid (PAA) and/or poly methacrylic acid (PMA).

In a preferred embodiment of the method of the present invention, wherein the crosslinking agent is selected from one of the group consisting of 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin and copolymer of dimethylamine and epichlorohydrin or a combination thereof.

In a preferred embodiment of the method of the present invention, wherein the concentration of the crosslinking agent is in the range of 100 ppm to 1000 ppm, and preferably in the range of 200 ppm to 600 ppm.

The method for manufacturing the ophthalmic lens of the present invention can further comprises a step of (d) conducting a sterilization treatment and a packing process to the lens body obtained from the step of (c). In a preferred embodiment of the manufacture method of the present invention, the resulted lens body obtained from the step of (c) is immersed in phosphate buffer solution to conduct a sterilization and packing process. In another preferred embodiment of the manufacturing method of the present invention, the solution containing the copolymer of carboxyl-containing polymer and zwitterionic polymer and the crosslinking agent in the step of (c) can be prepared with a phosphate buffer solution. The resulted lens body from the step of (b) is immersed in the solution containing the copolymer of carboxyl-containing polymer and zwitterionic polymer and the crosslinking agent prepared with phosphate buffer solution for a period of time and then, is sterilized and packed directly.

The above and other aspects of the invention will become better understood with regard to the following detailed description of the preferred but non-limiting embodiment(s). These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be affected without departing from the spirit and scope of the novel concepts of the disclosure.

DETAILED DESCRIPTION OF THE INVENTION

In the following detailed description, for purposes of explanation, numerous specific details are set forth in order to provide a thorough understanding of the disclosed embodiments. It will be apparent, however, that one or more embodiments may be practiced without these specific details.

It is apparent that departures from specific designs and methods described and shown will suggest themselves to those skilled in the art and may be used without departing from the spirit and scope of the invention. The present invention is not restricted to the particular constructions described and illustrated, but should be construed to cohere with all modifications that may fall within the scope of the appended claims.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

The invention, in one aspect, provides an ophthalmic lens comprising a lens body, a polydopamine layer and an antimicrobial layer. The visible light transmittance of the present ophthalmic lens is not less than 92%.

In an embodiment of the present invention, the lens body is made of a hydrogel material. The hydrogel material comprises but not limited to at least one hydrophilic monomer, a crosslinking agent and an initiator.

Suitable hydrophilic monomer can be, such as N-vinylpyrrolidone (NVP), 2-hydroxyethyl methacrylate (HEMA), N,N'-dimethylacrylamide (DMA), methyl acrylic acid (MAA), N,N'-diethylacrylamide, N-isopropylamide, 2-Hydroxypropyl acrylate, vinyl acetate, N-acrylolmorpholine, 2-dimethylaminoethyl acrylate or a combination thereof, but not limited thereto.

Suitable initiator can be the initiator suitably used in conventional ophthalmic lens materials, for example, thermal initiator or photo initiator. Suitable thermal initiator can be but not limited to, for example, 2,2'-azobis(2,4-dimethylvaleronitrile) (ADVN), 2,2'-azobis(isobutyronitrile) (AIBN), 2,2'-azobis(2,4-dimethylvaleronitrile), 2,2'-azobis (2-methyl-propanenitrile), 2,2'-azobis(2-methyl-butanenitrile) or benzoyl peroxide. Suitable photo initiator can be, but not limited to, for example, 2,4,6-trimethylbenzoyl diphenyl oxide, 2-hydroxy-2-methylpropiophenone, ethyl (2,4,6-trimethylbenzoly)phenylphosphinate or 2,2-diethoxyacetophenone.

Suitable crosslinking agent can be, for example, ethylene glycol dimethacrylate (EGDMA), trimethylolpropane trimethacrylate (TMPTA), triethylene ethylene glycol dimethacrylate (TEGDMA), tetraethylene ethylene glycol dimethacrylate (TrEGDMA), Poly(ethylene glycol) dimethacrylate, trimethylpropane trimethacrylate, vinyl methacrylate, ethylenediamine dimethyl acrylamide, glyceryl methacrylate, triallyisocyanurate, triallyl cyanurate or a combination thereof.

In another embodiment of the present invention, the lens body is made of silicone hydrogel. The silicone hydrogel can comprise but not limited to at least one siloxane macromer, at least one hydrophilic monomer and an initiator. Suitable siloxane macromer can be the siloxane macromer suitably used in conventional ophthalmic lens materials, particularly the siloxane macromers suitably used in conventional contact lens materials.

The silicone hydrogel can further include but not limited to a crosslinking agent, a dye, a UV-blocking agent, solvent or a combination thereof as needed. To simplify the description, the hydrophilic monomer, crosslinking agent and initiator mentioned above will not be described in detail herein.

The ophthalmic lens of the present invention comprises a polydopamine layer formed on the surface of the lens body and the polydopamine layer is adhered on the surface of the lens body. Polydopamine has adhesion property due to the catechol functional group thereof and can form covalent bond or non-covalent bond, such as hydrogen bond, van der Waals' force or a combination of stacking force, to a surface of a base material. Moreover, the polydopamine layer provides hydrophilic hydroxy functional groups and amine functional groups to the surface of lens body of the present invention, the hydrophilicity and chemical versatility of the lens body can be enhanced.

Although polydopamine has been widely used in surface modification of medical instrument for improving hydrophilicity, however, because polydopamine is in dark blue, the surface modified thereby will be in brown color. Thus, the conventional method for modifying surface of medical instrument by polydopamine is not suggested to be used on ophthalmic lens. The transmittance of the ophthalmic lens of the present invention can still be not less than 92% and thus the appearance and optical properties of the ophthalmic lens will not be affected by controlling the concentration of the polydopamine solution used in manufacturing process and manufacturing steps.

The antimicrobial layer is bonded to the polydopamine layer and formed from a copolymer of carboxyl-containing polymer and zwitterionic polymer and a crosslinking agent.

Suitable carboxyl-containing polymer can be but not limited to poly acrylic acid (PAA) and/or poly methacrylic acid (PMA).

The zwitterionic polymer is a polymer having both positively charged groups and negatively charged groups. Zwitterionic polymer has the properties of, such as, high hydrophilicity, good thermo- and chemical-stability, excellent biocompatibility and protein adhesion resistance. Therefore, deposit resistance and antimicrobial properties of the ophthalmic lens can be improved by modifying the surface of the ophthalmic lens with zwitterionic polymer. Suitable zwitterionic polymer can be but not limited to phosphorylcholine polymer, sulfobetaine polymer, carboxybetaine polymer, mixed-charge polymer or a combination thereof. In an embodiment of the present invention, the zwitterionic polymer can be poly(2-methacryloyloxyethyl phosphorylcholine) (PMPC), poly(sulfobetaine methacrylate) (PSBMA), poly(carboxybetaine methacrylate) (PCBMA) or a combination thereof.

Suitable crosslinking agent can be but not limited to 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin and copolymer of dimethylamine, epichlorohydrin or a combination thereof.

The weight average molecular weight of the copolymer of carboxyl-containing polymer and zwitterionic polymer is in the range of 10,000 to 500,000. In an embodiment of the present invention, the copolymer of carboxyl-containing polymer and zwitterionic polymer is the copolymer of poly acrylic acid and poly(sulfobetaine methacrylate) (PAA-co-PSBMA) and the weight average molecular weight of which is about 30,000.

Using the interaction between the crosslinking agent and the carboxyl functional group, the copolymer of carboxyl-containing polymer and zwitterionic polymer is thus bonded to the polydopamine layer of the ophthalmic lens of the present invention by the crosslinking agent. The thickness and density of the zwitterionic polymer can be increased by the interaction between the crosslinking agent and the carboxyl functional group. Due to the positive charge groups and negatively charged groups of the zwitterionic polymer, the deposition of protein, lipid and/or bacteria on the surface of the ophthalmic lens can be prevented. Moreover, polydopamine has excellent biocompatibility and hydrophilic function group, hydrophilicity of the ophthalmic lens can be enhanced therefore.

According to another aspect of the present invention, a method for manufacturing ophthalmic lens with excellent deposit resistance, high antimicrobial property, high hydrophilicity, desired optical properties and surface lubricity is provided. The present method can include but not limited to the following steps. The method for manufacturing ophthalmic lens has advantages of simple to produce and high effectively.

Firstly, a lens body is provided, which is made of a hydrogel or a silicon hydrogel. And then, the lens body is immersed in a polydopamine solution for coating a polydopamine layer on the surface of the lens body.

The polydopamine solution can be prepared, for example, by polymerizing a dopamine in alkaline aqueous solution to form the polydopamine solution. In an embodiment of the method of the present invention, the polydopamine solution is prepared by dissolving a dopamine in an aqueous sodium bicarbonate solution. In an embodiment of the method of the present invention, the concentration of the polydopamine solution is in the range of 50 ppm to 500 ppm, and preferably in the range of 50 ppm to 300 ppm. When the concentration of the polydopamine solution is higher than above mentioned range, the optical properties of the lens will be affected. When the concentration of the polydopamine solution is lower than above mentioned range, the polydopamine layer is formed insufficiently on the surface of the lens body for the zwitterionic polymer to be adhered thereon. In such a case, the deposit resistance and antimicrobial property of the ophthalmic lens is decreased.

In a preferred embodiment of the method of the present invention, when the lens body is immersed in the polydopamine solution, the polydopamine solution is heated at the temperature in the range of 40° C. to 80° C., and preferably in the range of 50° C. to 70° C. for a period of time in the range of 5 minutes to 60 minutes, and preferably in the range of 10 minutes to 30 minutes. When the lens body is immersed in the polydopamine solution, the time for immersing the lens body in the polydopamine solution or the heating temperature is higher than above mentioned range, the surface of the lens body will be brownish and thus, the light transmittance and the optical properties of the lens will be reduced. When the lens body is immersed in the polydopamine solution, the time for immersing the lens body in the polydopamine solution or the heating temperature is lower than above mentioned range, the polydopamine layer is formed insufficiently on the surface of the lens body for the zwitterionic polymer to be bonded thereon. In such a case, the deposit resistance, antimicrobial property and surface lubricity of the ophthalmic lens might be decreased.

After the polydopamine layer is coated on the lens body, the lens body is washed. In an embodiment of the method of the present invention, the polydopamine-coated lens body is washed by pure water to remove the residual polydopamine. The lens body is washed for about 5 minutes, but the time can be adjusted as needed.

After washing, the washed polydopamine-coated lens body is immersed in a solution containing a copolymer of carboxyl-containing polymer and zwitterionic polymer and a crosslinking agent to form an antimicrobial layer bonded to the polydopamine layer.

Suitable carboxyl-containing polymer can be, for example, poly acrylic acid (PAA), poly methacrylic acid (PMA) or a combination thereof.

Suitable zwitterionic polymer can be but not limited to phosphorylcholine polymer, sulfobetaine polymer, carboxybetaine polymer, mixed-charge polymer or a combination thereof.

In an embodiment of the method of the present invention, the zwitterionic polymer can be poly(2-methacryloyloxyethyl phosphorylcholine) (PMPC), poly(sulfobetaine methacrylate) (PSBMA), poly(carboxybetaine methacrylate) (PCBMA) or a combination thereof, but not limited thereto.

In an embodiment of the method of the present invention, the copolymer of carboxyl-containing polymer and zwitterionic polymer can be the copolymer of poly acrylic acid and poly(sulfobetaine methacrylate) (PAA-co-PSBMA). In an embodiment of the method of the present invention, the weight average molecular weight of the copolymer of carboxyl-containing polymer and zwitterionic polymer is in the range of 10,000 to 50,000, and preferably in the range of 20,000 to 40,000. The concentration of the copolymer of carboxyl-containing polymer and zwitterionic polymer is in the range of 200 ppm to 2000 ppm, and preferably in the range of 300 ppm to 1000 ppm.

Suitable crosslinking agent can be, for example, 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin, copolymer of dimethylamine and epichlorohydrin or a combination thereof, but not limited thereto. In an embodiment of the method of the present invention, the crosslinking agent can be 1,4-butanediol diglycidyl ether (BDDE). The concentration of the crosslinking agent is in the range of 100 ppm to 1000 ppm, and preferably in the range of 200 ppm to 600 ppm.

In a preferred embodiment of the method of the present invention, when the polydopamine-coated lens body is immersed in the solution containing copolymer of carboxyl-containing polymer and zwitterionic polymer and the crosslinking agent, solution containing copolymer of carboxyl-containing polymer and zwitterionic polymer and the crosslinking agent can be heated at the temperature in the range of 60° C. to 121° C., and preferably in the range of 70° C. to 121° C. The time for immersing the polydopamine-coated lens body in the solution containing the copolymer of carboxyl-containing polymer and zwitterionic polymer and the crosslinking agent is in the range of 20 minutes to 90 minutes, and preferably in the range of 30 minutes to 60 minutes. As the heating temperature is higher than the above mentioned range and/or the time for immersing the polydopamine-coated lens body therein is longer than the above mentioned range, the optical property of the ophthalmic lens will be affected. As the heating temperature is lower than the above mentioned range and/or the time for immersing the polydopamine-coated lens body therein is shorter than the above mentioned range, the deposit resistance and antimicrobial property of the ophthalmic lens will be affected.

After the polydopamine-coated lens body is immersed in the solution containing the copolymer of carboxyl-containing polymer and zwitterionic polymer and the crosslinking agent for bonding the copolymer of carboxyl-containing polymer and zwitterionic polymer to the polydopamine layer to form the antimicrobial layer, a sterilization treatment can be conducted to the lens body. The sterilization treatment suitably used in conventional method for manufacturing contact lenses can be used in the method of the present invention.

In an embodiment of the method of the present invention, the solution containing the copolymer of carboxyl-containing polymer and zwitterionic polymer and the crosslinking agent is prepared with deionized water, after taking out the lens body from the solution containing the copolymer of carboxyl-containing polymer and zwitterionic polymer and the crosslinking agent, the lens body is then immersed in a phosphate buffer solution to conduct a sterilization treatment and packing process. In another embodiment of the method of the present invention, the solution containing the copolymer of carboxyl-containing polymer and zwitterionic polymer and the crosslinking agent is prepared with a phosphate buffer solution, after immersing the lens body in the phosphate buffer solution containing copolymer of carboxyl-containing polymer and zwitterionic polymer and the crosslinking agent, a sterilization treatment and packing process are conducted directly.

Accordingly, the method for manufacturing ophthalmic lens of the present invention can be introduced into conventional method for manufacturing contact lens, the antimicrobial layer can bond to the polydopamine layer of the surface of the ophthalmic lens during lens sterilization treatment and packing process to simplify the surface modification of the lens therefore.

In comparison to the conventional surface modified process for medical equipment, the method of the present invention comprises the steps of immersing the lens body in the polydopamine solution, washing the polydopamine-coated lens body, and then, immersing the polydopamine-coated lens body in the solution containing copolymer of carboxyl-containing polymer and zwitterionic polymer and the crosslinking agent. The density of the zwitterionic polymer of the ophthalmic lens manufactured by the method of the present invention can be increased, thus, the ophthalmic lens manufactured by the method of the present invention has excellent deposit resistance, high antimicrobial property, high hydrophilicity and great surface lubricity, and suitable transmittance and desired optical properties can still be retained by reducing the concentration of the polydopamine solution used in the manufacturing process.

The present invention will be explained in further detail with reference to the examples. However, the present invention is not limited to these examples.

PREPARATION EXAMPLE 1

The Preparation of Polydopamine Solution 1 g of dopamine was dissolved in 1000 ml of aqueous sodium bicarbonate solution (pH is 8.5) and stirred for 24 hours. The resulting polydopamine solution with a concentration of 1000 ppm was obtained.

PREPARATION EXAMPLE 2

The Preparation of Silicon Hydrogel Lens Body 4.44 g of isophorone diisocyanate, 0.0025 g of dibutyltin dilaurate as the catalysts, and 40 mL of methylene chloride were added into a flask to form a solution, and the solution was stirred under a stream of nitrogen. Then, 20 g of α-butyl-ω-[3-(2,2-(hydroxymethyl) butoxy) propyl] polydimethylsiloxane was accurately weighed and added dropwise to the solution over about 1 hour. After the solution reacting at room temperature for 12 hours, the resulting reaction product was washed with a large amount of water, and then dehydrated and filtered to obtain a raw product. Then, the methylene chloride was evaporated to obtain a first siloxane macromer.

8.88 g of isophorone diisocyanate, 0.0025 g of dibutyltin dilaurate as the catalysts and 40 mL of methylene chloride were added into a flask to form a solution, and the solution was stirred under a stream of nitrogen. Then, 20 g of polydimethylsiloxane was accurately weighed and added dropwise to the solution over about 1 hour. After the solution reacting at room temperature for 12 hours, another 0.0025 g of dibutyltin dilaurate and 14.4 g of polyethylene glycol monomethacrylate were accurately weighed and added dropwise to the solution over about 1 hour. After the solution reacting at room temperature for another 12 hours, the resulting reaction product was washed with a large amount of water, and then dehydrated and filtered to obtain a raw product. Then, the methylene chloride was evaporated to obtain a second siloxane macromer.

41.8 g of the first siloxane macromer, 6.3 g of the second siloxane macromer, 0.7 g of azobisisoheptonitrile (ADVN), 46.96 g of N-vinylpyrrodine (NVP), 6.3 g of 2-hydroxyethyl methacrylate (HEMA), 1 g of ethylene glycol dimethylacrylate (EGDMA) and 25.1 g of hexanol were mixed and stirred about 1 hour to form a mixture. Then, the mixture was injected into a mold of contact lens made of polypropylene (PP) and heated to initiate the radical polymerization thereof at 60° C. for 1 hour, 80° C. for 2 hours and 135° C. for 2 hours. After the polymerization was completed, the mold was immersed in 80% alcohol solution for 1 hour and the resulting molded lens was taken out of the mold to obtain a silicon hydrogel lens body.

EXAMPLE 1

First, the concentration of the polydopamine solution of preparation example 1 was diluted with aqueous sodium bicarbonate solution (pH is 8.5) to 100 ppm. Then, the silicon hydrogel lens body of preparation example 2 was immersed in the diluted polydopamine solution at 50 L for 10 minutes and washed by water.

And then the silicon hydrogel lens body was immersed in the aqueous solution containing 500 ppm poly(sulfobetaine methacrylate) and 250 ppm 1,4-butanediol diglycidyl ether at 80° C. for 60 minutes and washed by water to obtain the ophthalmic lens. The results of optical property, physical property, and antimicrobial tests of the ophthalmic lens were shown as the following Table 1.

EXAMPLE 2

First, the concentration of the polydopamine solution of preparation example 1 was diluted with aqueous sodium bicarbonate solution (pH is 8.5) to 100 ppm. Then, the silicon hydrogel lens body of preparation example 2 was immersed in the diluted polydopamine solution at 50° C. for 00 minutes and washed by water.

And then the silicon hydrogel lens body was immersed in the aqueous solution containing 1000 ppm poly(sulfobetaine methacrylate) and 250 ppm 1,4-butanediol diglycidyl ether at 80° C. for 60 minutes and washed by water to obtain the ophthalmic lens. The results of optical property, physical property, and antimicrobial tests of the ophthalmic lens were shown as the following Table 1.

EXAMPLE 3

First, the concentration of the polydopamine solution of preparation example 1 was diluted with aqueous sodium bicarbonate solution (pH is 8.5) to 100 ppm. Then, the silicon hydrogel lens body of preparation example 2 was immersed in the diluted polydopamine solution at 50° C. for 10 minutes and washed by water.

And then the silicon hydrogel lens body was immersed in the aqueous solution containing 1000 ppm poly(sulfobetaine methacrylate) and 500 ppm 1,4-butanediol diglycidyl ether at 80° C. for 60 minutes and washed by water to obtain the ophthalmic lens. The results of optical property, physical property, and antimicrobial tests of the ophthalmic lens were shown as the following Table 1.

EXAMPLE 4

First, the concentration of the polydopamine solution of preparation example 1 was diluted with aqueous sodium bicarbonate solution (pH is 8.5) to 100 ppm. Then, the silicon hydrogel lens body of preparation example 2 was immersed in the diluted polydopamine solution at 50° C. for 10 minutes and washed by water.

And then the silicon hydrogel lens body was immersed in the aqueous solution containing 1000 ppm poly(sulfobetaine methacrylate) and 200 ppm 1,4-butanediol diglycidyl ether at 80° C. for 60 minutes and washed by water to obtain the ophthalmic lens. The results of optical property, physical property, and antimicrobial tests of the ophthalmic lens were shown as the following Table 1.

EXAMPLE 5

First, the concentration of the polydopamine solution of preparation example 1 was diluted with aqueous sodium bicarbonate solution (pH is 8.5) to 100 ppm. Then, the silicon hydrogel lens body of preparation example 2 was immersed in the diluted polydopamine solution at 50° C. for 10 minutes and washed by water.

And then the silicon hydrogel lens body was immersed in the aqueous solution containing 500 ppm poly(sulfobetaine methacrylate) and 100 ppm 1,4-butanediol diglycidyl ether at 80° C. for 60 minutes and washed by water to obtain the ophthalmic lens. The results of optical property, physical property, and antimicrobial tests of the ophthalmic lens were shown as the following Table 1.

EXAMPLE 6

First, the concentration of the polydopamine solution of preparation example 1 was diluted with aqueous sodium bicarbonate solution (pH is 8.5) to 100 ppm. Then, the silicon hydrogel lens body of preparation example 2 was immersed in the diluted polydopamine solution at 50° C. for 10 minutes and washed by water.

And then the silicon hydrogel lens body was immersed in the aqueous solution containing 1000 ppm poly(sulfobetaine methacrylate) and 500 ppm 1,4-butanediol diglycidyl ether at 80° C. for 60 minutes and washed by water to obtain the ophthalmic lens. The results of optical property, physical property, and antimicrobial tests of the ophthalmic lens were shown as the following Table 1.

COMPARATIVE EXAMPLE 1

The Comparative Example 1 was the silicone hydrogel lens body of Preparation Example 2, the surface of the lens body did not comprise the polydopamine layer and the antimicrobial layer. The results of optical property, physical property, and antimicrobial tests of the ophthalmic lens were shown as the following Table 1.

Measurement of the Visible Light Transmittance of Ophthalmic Lens

The transmittance of visible light with wavelength of 370 nm-780 nm of the ophthalmic lens was measured by UV-Visible Spectrophotometer (V-650, commercially available from JASCO, Japan).

Measurement of the Water Content of Ophthalmic Lens

The ophthalmic lens was immersed in the phosphate buffered saline (PBS) at 23° C. for 24 hours. Then, the ophthalmic lens was removed therefrom and was taken to remove all surface water by long-fiber cloth. After that, the weight of ophthalmic lens W1 was measured. Next, the ophthalmic lens was dried at 600 W for 5 minutes by microwave and after that the weight of hydrated ophthalmic lens W2 was measured. The water contact of ophthalmic lens was calculated by the following equation:

$$(W1-W2)/W1 \times 100\%.$$

Measurement of Contact Angle

The ophthalmic lens was immersed in water for 1 hour. Then, the ophthalmic lens was removed therefrom and was taken to remove all surface water by wet wipe. After that, the contact angle of ophthalmic lens was measured by Contact Angle Wafer Surface Analysis Inspection Goniometer (VCA2500XE, commercially available from AST Products, USA).

Measurement of Oxygen Permeability

The oxygen permeability (Dk) was measured according to ISO standards 18369-4:2006, 4.4.3, by using an oxygen permeability tester (201T). The units of oxygen permeability (Dk) is defined as $10^{-10}$ $(mlO_2$ mm$)/(cm^2$ sec mm Hg$)$.

Test of Surface Lubricity

The ophthalmic lens was immersed in water for 1 hour. Then, the ophthalmic lens was removed therefrom and was taken to remove all surface water by wipe. After that, the ophthalmic lens was immersed in the Sudan Black B Stain for 5 minutes. Next, the ophthalmic lens was removed therefrom and washed both surface of the ophthalmic lens by water for 2 minutes. After air drying, the ophthalmic lens was observed by eyes. The surface of the ophthalmic lens is hydrophobic and the surface lubricity is poor when the appearance of the ophthalmic lens is dark blue, and the surface of the ophthalmic lens is hydrophilic and the surface lubricity is good when the ophthalmic lens is transparent.

Measurement of Protein Adhesion

The ophthalmic lens was immersed in water for 1 hour. Then, the ophthalmic lens was removed therefrom and was taken to remove all surface water by wet wipe. After that, the ophthalmic lens was immersed in a PP sample tube containing 3 ml of lysozyme solution and the PP sample tube was sealed by a PP protective cap and incubated at 37° C. for 48 hours. Next, the ophthalmic lens was removed therefrom and was taken to remove all surface lysozyme solution by wet wipe. And then, the ophthalmic lens was immersed in a PP sample tube containing 2 ml lens extraction solution (the volume ratio of trifluoroacetic acid/acetonitrile/water was 1/500/500), and the sample tube was rotated by a rotary oscillator at 37° C. for 12 hours. In final, the ophthalmic lens was removed therefrom and the protein adhesion was determined by measuring the weight of protein in the extraction solution.

Measurement of Lipid Adhesion

The ophthalmic lens was immersed in water for 1 hour. Then, the ophthalmic lens was removed therefrom and was taken to remove all surface water by wet wipe. After that, the ophthalmic lens was immersed in a PP sample tube containing 3 ml of cholesterol solution and the PP sample tube was sealed by a PP protective cap and incubated at 37° C. for 48 hours. Next, the ophthalmic lens was removed therefrom and was taken to remove all surface cholesterol solution by wet wipe. And then, the ophthalmic lens was immersed in a PP sample tube containing 2 ml lens extraction solution (the volume ratio of trichloromethane/Methanol was 2/1), and the sample tube was rotated by a rotary oscillator at 37° C. for 12 hours. In final, the ophthalmic lens was removed therefrom and absorbance value was measured. The lipid adhesion of each lens was determined according to the lipid standard curve made from standard lipid concentration and absorbance value.

6 are about 131 to 133. It can be seen that the desirable optical and physical properties of ophthalmic lens can still be retained.

While the invention has been described by way of example(s) and in terms of the embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A contact lens, comprising:
    a lens body;
    a polydopamine layer formed on the surface of the lens body by immersing the lens body in a polydopamine solution prepared from dopamine in alkaline environments and heating at the temperature in the range of 40° C. to 80° C. for a period of time in the range of 5 minutes to 60 minutes; and
    an antimicrobial layer bonded to the polydopamine layer and formed from a copolymer of carboxyl-containing polymer and zwitterionic polymer and a crosslinking agent, wherein the zwitterionic polymer is selected from one of the group consisting of phosphorylcholine polymer, sulfobetaine polymer, carboxybetaine polymer and mixed-charge polymer or a combination thereof;
    wherein the polydopamine layer is substantially colorless on the contact lens; and
    wherein the visible light transmittance of the contact lens is not less than 92%.

2. The contact lens according to claim 1, wherein the zwitterionic polymer is selected from one of the group consisting of poly(2-methacryloyloxyethyl phosphorylcho-

TABLE 1

The measurement results of Example 1 - Example 6 and Comparative Example 1

|  | Example | | | | | | Comparative Example |
| --- | --- | --- | --- | --- | --- | --- | --- |
|  | 1 | 2 | 3 | 4 | 5 | 6 | 1 |
| Visible light transmittance (%) | 92 | 92 | 92 | 92 | 92 | 92 | 98 |
| Contact angle (°) | 18.7 | 17.6 | 18.5 | 16.9 | 18.2 | 17.9 | 97.4 |
| Water content (%) | 44.9 | 45.1 | 45.2 | 44.8 | 45.0 | 44.9 | 45.2 |
| Oxygen permeability | 130 | 132 | 132 | 133 | 131 | 131 | 131 |
| Surface lubricity | Good | Good | Good | Good | Good | Good | Poor |
| Protein adhesion (μg) | 11.22 | 15.44 | 10.22 | 14.49 | 15.67 | 12.21 | 18.1 |
| Lipid adhesion (μg) | 3.75 | 4.01 | 3.62 | 3.98 | 4.91 | 3.56 | 5.37 |

From the results shown in Table 1, the protein adhesions of Example 1 to Example 6 are all less than 16 μg and the lipid adhesions thereof all less than 5 μg. Therefore, Examples 1 to Example 6 of the present invention have more excellent deposit resistance than Comparative Example 1. In addition, the contact angles of Example 1 to Example 6 are all less than 20°, and the appearance of the ophthalmic lens are transparent after test of surface lubricity, the ophthalmic lens of the present invention has high hydrophilicity and good surface lubricity. Moreover, the visible light transmittances of Example 1 to Example 6 are not less than 92%, the water contents of Example 1 to Example 6 are about 44.8% to 45.2, the oxygen permeabilities of Example 1 to Example line) (PMPC), poly(sulfobetaine methacrylate) (PSBMA) and poly(carboxybetaine methacrylate) (PCBMA) or a combination thereof.

3. The contact lens according to claim 1, wherein a weight average molecular weight of the copolymer of carboxyl-containing polymer and zwitterionic polymer is in the range of 10,000 to 500,000.

4. The contact lens according to claim 1, wherein the carboxyl-containing polymer is poly acrylic acid (PAA) and/or poly methacrylic acid (PMA).

5. The contact lens according to claim 1, wherein the crosslinking agent is selected from one of the group consisting of 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin and copolymer of dimethylamine and epichlorohydrin or a combination thereof.

6. The contact lens according to claim 1, wherein the lens body is made of a hydrogel or a silicon hydrogel.

7. A method for manufacturing a contact lens, comprising steps of:
   (a) providing a lens body, and immersing the lens body in a polydopamine solution prepared from dopamine in alkaline environments and heating at the temperature in the range of 40° C. to 80° C. for a period of time in the range of 5 minutes to 60 minutes to coat a polydopamine layer on a surface of the lens body;
   (b) washing the polydopamine-coated lens body; and
   (c) immersing the polydopamine-coated lens body in a solution containing a copolymer of carboxyl-containing polymer and zwitterionic polymer and a crosslinking agent to form an antimicrobial layer bonded to the polydopamine layer;
   wherein the zwitterionic polymer is selected from one of the group consisting of phosphorylcholine polymer, sulfobetaine polymer, carboxybetaine polymer and mixed-charge polymer or a combination thereof;
   wherein the polydopamine layer is substantially colorless on the contact lens; and
   wherein the visible light transmittance of the contact lens is not less than 92%.

8. The method for manufacturing the contact lens according to claim 7, wherein the zwitterionic polymer is selected from one of the group consisting of poly(2-methacryloyloxyethyl phosphorylcholine) (PMPC), poly(sulfobetaine methacrylate) (PSBMA) and poly(carboxybetaine methacrylate) (PCBMA) or a combination thereof.

9. The method for manufacturing the contact lens according to claim 7, wherein the concentration of the polydopamine solution is in the range of 25 ppm to 500 ppm.

10. The method for manufacturing the contact lens according to claim 7, wherein the concentration of the copolymer of carboxyl-containing polymer and zwitterionic polymer is in the range of 200 ppm to 2000 ppm.

11. The method for manufacturing the contact lens according to claim 7, wherein the solution containing copolymer of carboxyl-containing polymer and zwitterionic polymer and the crosslinking agent is heated at the temperature in the range of 60° C. to 121° C. in the step of (c).

12. The method for manufacturing the contact lens according to claim 7, wherein the polydopamine-coated lens body is immersed in the solution containing the copolymer of carboxyl-containing polymer and zwitterionic polymer and the crosslinking agent for a time in the range of 20 minutes to 90 minutes in the step of (c).

13. The method for manufacturing the contact lens according to claim 7, wherein the weight average molecular weight of the copolymer of carboxyl-containing polymer and zwitterionic polymer is in the range of 10,000 to 50,000.

14. The method for manufacturing the contact lens according to claim 7, wherein the carboxyl-containing polymer is poly acrylic acid (PAA) and/or poly methacrylic acid (PMA).

15. The method for manufacturing the contact lens according to claim 7, wherein the concentration of the crosslinking agent is in the range of 100 ppm to 1000 ppm.

16. The method for manufacturing the contact lens according to claim 7, wherein the crosslinking agent is selected from one of the group consisting of 1,4-butanediol diglycidyl ether (BDDE), polyethylene glycol diacrylate (PEGDA), ethylene glycol diglycidyl ether, 1,6-hexanediol diglycidyl ether, polypropylene glycol diglycidyl ether, polytetramethylene glycol diglycidyl ether, neopentyl glycol diglycidyl ether, polyglycerol polyglycidyl ether, diglycerolpolyglycidyl ether, glycerol polyglycidyl ether, tri-methylolpropanepolyglycidyl ether, pentaerythritolpolyglycidyl ether, sorbitol polyglycidyl ether, 1,2,7,8-diepoxyoctane, 1,3-butadiene diepoxide, polyamidoamineepichlorohydrin and copolymer of dimethylamine and epichlorohydrin or a combination thereof.

* * * * *